United States Patent [19]
Gipson, II

[11] Patent Number: 5,882,613
[45] Date of Patent: Mar. 16, 1999

[54] TOOTHBRUSH HOLDER AND SANITIZER FLUSH APPARATUS

[76] Inventor: Lovelace Preston Gipson, II, 1040 Twinkletown Rd., Memphis, Tenn. 38116

[21] Appl. No.: 13,941

[22] Filed: Jan. 27, 1998

[51] Int. Cl.⁶ ..................................................... A61L 2/18
[52] U.S. Cl. ...................... 422/300; 422/292; 206/209.1; 206/368; 132/308; 132/313
[58] Field of Search ............................... 422/28, 292, 294, 422/300, 301; 206/209.1, 368, 369; 132/308, 313

[56] References Cited

U.S. PATENT DOCUMENTS

| | | | |
|---|---|---|---|
| 1,283,403 | 10/1918 | Eustis | 422/300 |
| 1,743,646 | 1/1930 | Alderman, Jr. | 206/209.1 |
| 5,086,916 | 2/1992 | Gray | 422/300 |
| 5,402,810 | 4/1995 | Donley | 206/209.1 |
| 5,471,706 | 12/1995 | Wallock et al. | 15/302 |
| 5,722,537 | 3/1998 | Sigler | 422/300 |

*Primary Examiner*—Krisanne Thornton
*Assistant Examiner*—Fariborz Moazzam
*Attorney, Agent, or Firm*—John J. Mulrooney

[57] ABSTRACT

A toothbrush sterilizing container for holding and sterilizing the bristles and handle of a toothbrush includes a storage canister for receiving and holding the bristles of a toothbrush immersed in a sterilizing solution while the toothbrush handle extends through the open top end of the canister. A reservoir of sterilizing solution supplies fresh solution to the canister and a spout allows used solution to be drained from the canister. A lid has a slot for receiving the toothbrush handle and a supply of disinfectant in the lid maintains the handle in a sterile environment.

20 Claims, 3 Drawing Sheets

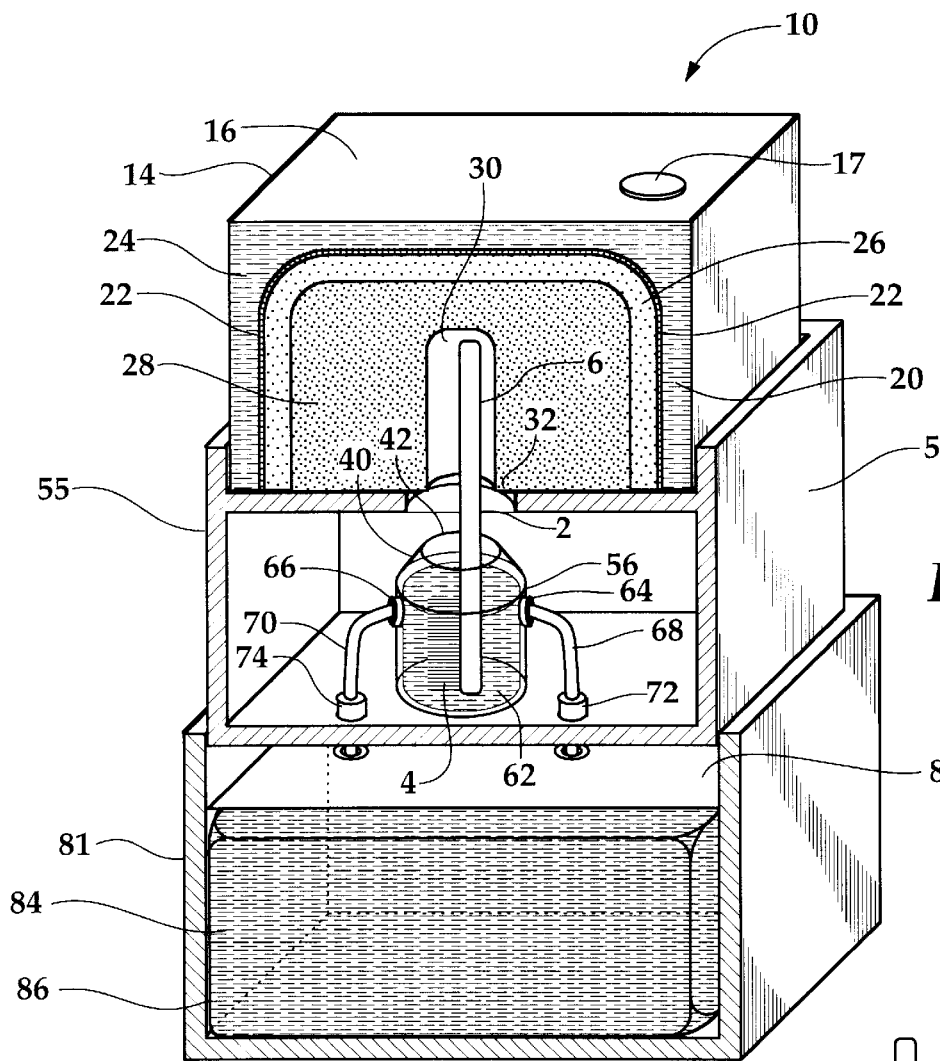
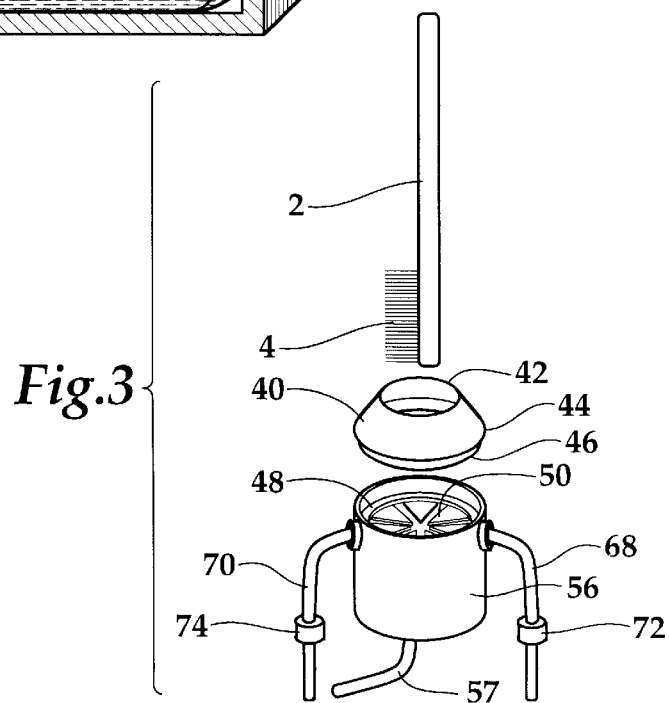
*Fig.2*
*Fig.3*

TOOTHBRUSH HOLDER AND SANITIZER FLUSH APPARATUS

BACKGROUND OF THE INVENTION

1. Field of the Invention

This invention relates to apparatus for storing and sanitizing toothbrushes between uses and, more particularly, to a holder useful to store toothbrush bristles in individual canisters containing sterilizing solution which may be flushed by removing used sterilizing solution and adding fresh sterilizing solution, and having a lid for storing the toothbrush handle in a sterile environment.

2. Description of the Prior Art

Toothbrushes are customarily stored when not in use in relatively unsanitary conditions. For example, after being used, toothbrushes are typically stored uncovered on shelves or in non-sanitized holders where they are exposed to any insects and germs or contaminants in the air. Toothbrushes stored in this manner are wet and possibly contain germs and food particles from the user's mouth, which are conditions that attract insects and promote the growth of bacteria and the spread of germs.

The problem of unsanitary storage of toothbrushes has been recognized, and toothbrush holders which perform a sanitizing function by exposing the bristles of the brush to a germicidal agent are known in the art. Examples of such prior art are the disclosures in U.S. Pat. Nos. 5,086,916 and 4,585,119. In spite of these prior attempts to remedy the problem of unsanitary storage, studies show that unsanitary storage of toothbrushes remains the norm. This suggests that the prior art attempts at solutions have been defective in some way or unacceptable to toothbrush users for some reason.

An object of this invention is to improve the apparatus of toothbrush sanitizing holders.

A further object of this invention is to a provide a toothbrush sanitizing holder which is both simple and user friendly in its method of operation so as to promote the use of toothbrush sanitizing holders among toothbrush users.

A further object of this invention is to a provide a toothbrush sanitizing holder which has individual storage chambers for preventing cross-contamination by direct contact between the individual toothbrushes.

A further object of this invention is to provide a sterilizing toothbrush holder having a flush feature to facilitate the removal of used sterilizing solution and the addition of fresh sterilizing solution.

A further object of the invention is to provide a toothbrush sanitizing holder having a replaceable reservoir of sterilizing solution of known and constant strength for repeatedly replenishing the solution in the storage chambers with solution of known and constant efficacy.

A further object of the invention is to provide a toothbrush sanitizing holder which stores both the bristles and handle of the toothbrush in sterile environments while preventing the evaporation and contamination of the sterilizing solution.

SUMMARY OF THE INVENTION

Briefly stated, the objects are accomplished by a toothbrush holder useful for simultaneously storing and sanitizing toothbrushes between uses, and which is capable of being flushed by draining used sterilizing solution while simultaneously or subsequently adding fresh sterilizing solution. The holder may be used as a self-standing apparatus on a horizontal surface or may be mounted on a vertical surface. The holder consists of a toothbrush storage compartment having a storage canister for receiving and exposing the bristles of a toothbrush to a sanitizing solution. A reservoir of sanitizing solution is connected to the canister by fluid lines having unidirectional flow valves therein which permit solution to be transferred from the reservoir to the canister, but do not permit used solution to flow from the canister to the reservoir. The flushing of the individual canisters is accomplished by draining used sterilizing solution from the canister through a drain spout while either simultaneously or subsequently and independently adding fresh sterilizing solution from the reservoir. A removable lid with an elongated slot receives and holds the toothbrush handle in a sanitary environment and provides a closure for the toothbrush storage compartment. A viscous disinfectant in the lid is transported by an absorbent material to the slot where the handle is maintained in a sterile environment.

BRIEF DESCRIPTION OF THE DRAWINGS

A more complete understanding of the invention may be obtained by reference to the accompanying drawings wherein:

FIG. 2 is a perspective view partially broken away of the invention.

FIG. 3 is an exploded view of an assembly comprising the toothbrush 2, the toothbrush alignment member 40, the toothbrush flexing member 48, the bristle contacting element 50, and the canister 56 with the drain spout 57.

DESCRIPTION OF THE PREFERRED EMBODIMENTS

Figure 1A:
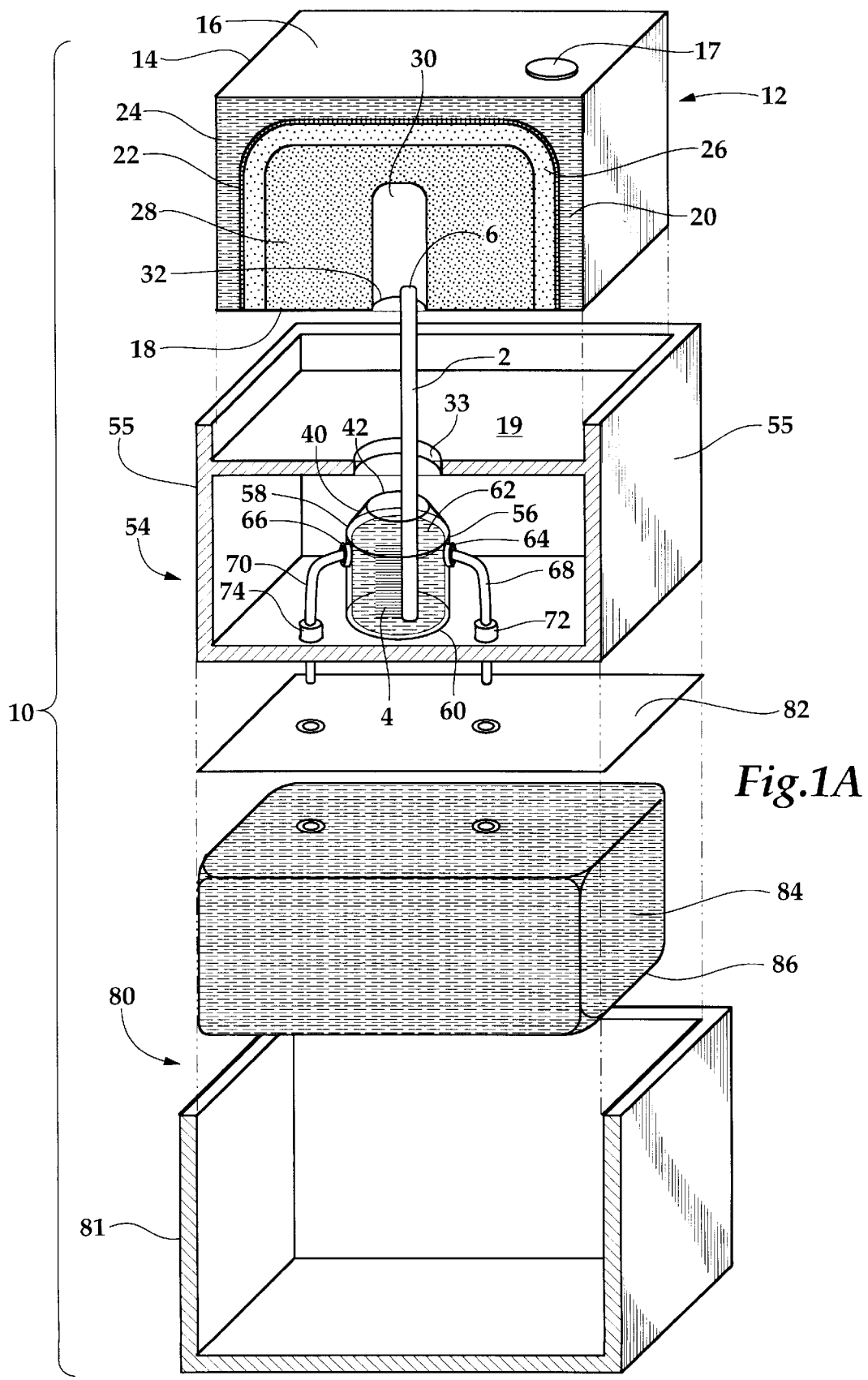
FIG. 1A is an exploded, perspective view partially broken away of the invention.

Referring to the drawings, a toothbrush holder and sanitizing apparatus 10 according to the present invention has a removable lid 12 in the form of a housing 14 having a top surface 16, front, back and side surfaces (not numbered), and a bottom surface 18. A chamber 20 in lid 12 stores a supply of a viscous disinfectant 24, and chamber 20 has a porous or permeable wall 22 which permits the disinfectant 24 to escape by seepage at a slow rate. In an alternative embodiment, chamber 20 is a prepackaged container having porous walls and which is filled with a viscous disinfectant. A first sponge or similar absorbent material 26 abuts the porous wall 22 and absorbs the viscous disinfectant 24 which seeps through porous wall 22. A second sponge or similar absorbent, pliable material 28 abuts first sponge 26 and has a slot 30 which is adapted to receive the handle 6 of toothbrush 2. First sponge 26 and second sponge 28 function to transport the absorbed viscous disinfectant 24 from chamber 20 to slot 30 where the toothbrush handle 6 will be exposed to disinfectant 24 and maintained in a sanitary environment. Sponge 28 is flexible and pliable so as to accommodate the variations in the shapes of toothbrush handles. The bottom surface 18 of lid housing 14 has an opening 32 which is aligned with toothbrush handle slot 30.

The preferred viscous disinfectant 24 is a hypo chlorite, however, alternatives such as alcohol or any commercially available disinfectant non-injurious to oral tissues could be used to obtain the desired results. An input port 17 in housing top surface 16 permits the supply of viscous disinfectant 24 to be replenished. An alternative embodiment to the disinfectant chamber 20 having a permeable wall which permits disinfectant to escape by seepage can be a supply of disinfectant in a porous package which is in contact with the first sponge 26.

A toothbrush aligning member 40 is positioned below bottom surface 18 of lid 12. Member 40 has a generally cylindrical shape with a top opening 42, a lower rim 44 and a bottom opening 46 having a circumference smaller than that of rim 44. Top opening 42 will be aligned with opening 32 in bottom surface 18. The lower rim 44 of member 40 will rest on the top of a toothbrush storage canister 56 and bottom opening 46 will fit into the top of canister 56.

Referring to FIG. 3, a ring shaped element 48 is aligned with member 40 and canister 56. Element 48 has a flexing member 50 which is designed to contact and flex the bristles 4 to remove particles of food from the bristles each time the toothbrush is inserted or withdrawn from the storage compartment 54. Member 50 may consist of bristles or a flexible rubber insert in element 48. It will be recognized that flexing member 48 may be positioned in alignment member 40 or in canister 56, or in between alignment member 40 and canister 56.

A toothbrush storage compartment 54 consists of a canister 56 having a top opening 58 and a closed bottom 60. A quantity of sterilizing solution 62 in canister 56 covers the bristles 4 of toothbrush 2 and the toothbrush handle 6 extends through the top opening 58. Canister 56 has first and second sanitizing solution input ports 64 and 66, preferably positioned on canister 56 above the point to which the canister will be filled with sanitizing solution.

First and second sanitizing solution supply lines 68 and 70 connect the ports 64 and 66 on canister 56 to a sanitizing solution reservoir 80 and function as fluid conduits to transport sterilizing solution from reservoir 80 to canister 56. The canister 56 has a spout 57 (FIG. 3) which is normally closed but which may be opened to permit the canister to be flushed by the removal of used sterilizing solution through spout 57 and the addition of fresh sterilizing solution through solution supply lines 68 and 70. Unidirectional flow valves 72 and 74 in lines 68 and 70 permit sterilizing solution to flow from the reservoir 80 to canister 56, but prevent the flow of used sterilizing solution from canister 56 to reservoir 80.

The toothbrush storage compartment 54 has a shelf 19 on which the lid housing 14 sits (see FIG. 2), and shelf 19 has an opening 33 therein which is aligned with the toothbrush handle slot 30, the bottom opening 32 in lid 12, and opening 42 of the toothbrush aligning member 40. The toothbrush storage compartment 54 has lateral sides 55 which receive and support the lid housing 14 and which extend downwardly to engage and rest on a pressure plate 82 which forms the top surface of a reservoir housing 81.

A sterilizing solution reservoir 80 consists of a housing 81 having a depressable top side pressure plate 82. Housing 81 is designed to receive and hold a supply of sanitizing solution 84. Fluid supply lines 68 and 70 are connected through pressure plate 82 to the supply of sanitizing solution 84. In a first embodiment (FIG. 1A), the housing 81 receives a plastic bag or similar pre-filled, deformable container 86 of sterilizing solution 84. The bag 86 is connected to supply lines 68 and 70 and application of pressure on plate 82 causes the solution in bag 86 to be forced through lines 68 and 70 into canister 56. In an alternative embodiment, the housing 81 is designed to hold the sanitizing solution and is filled with sanitizing solution 84, whereby pressure exerted on reservoir housing top side 82 exerts pressure on the sanitizing solution 84 in housing 81 to force the solution to flow through supply conduits 68 and 70 into canister 56.

Figure 1B:
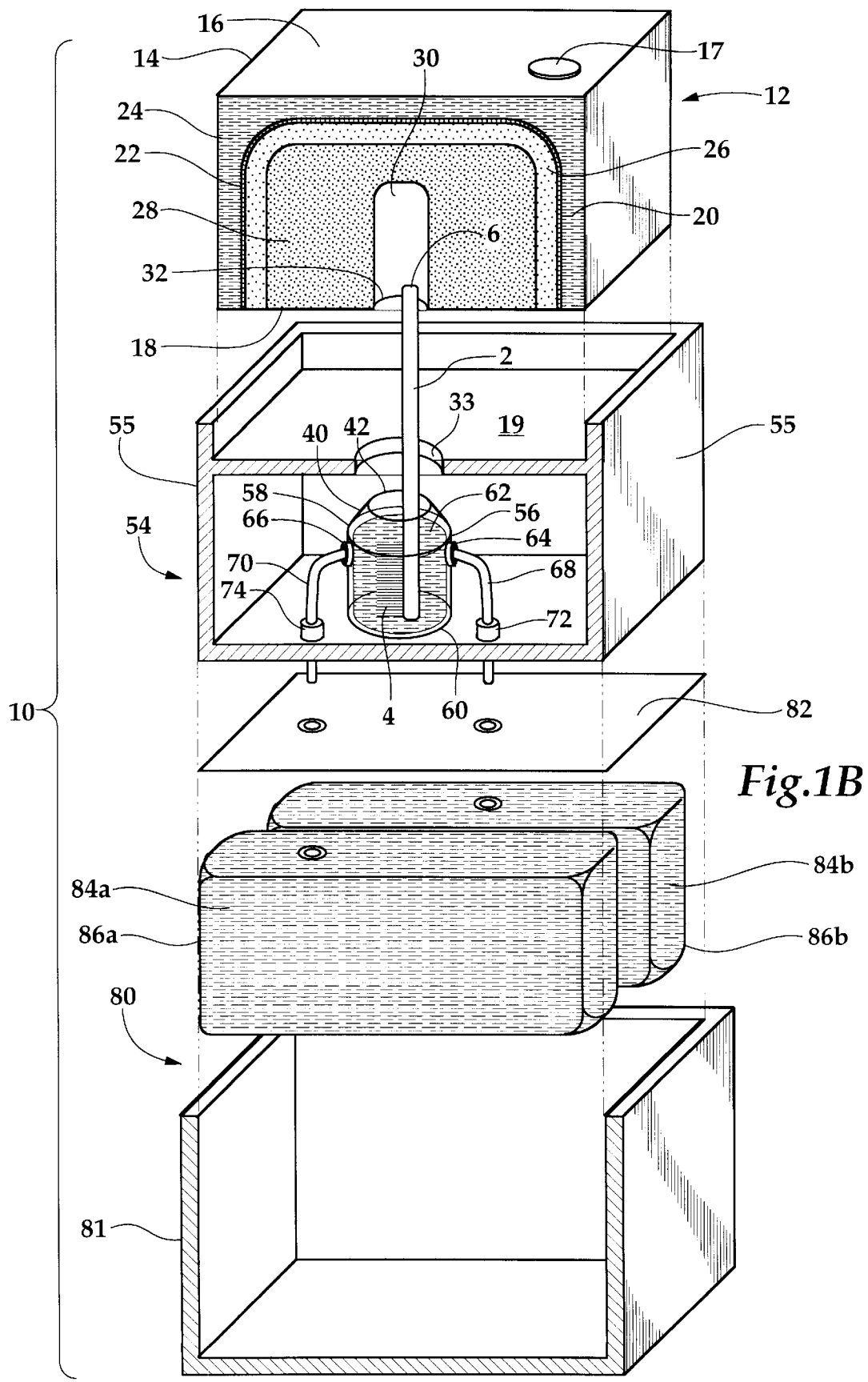
FIG. 1B is an exploded, perspective view partially broken away of another embodiment of the invention.

In a third embodiment (FIG. 1B), the single deformable container 86 of sterilizing solution 84 is replaced by 2 pre-filled, deformable containers 86a and 86b which contain different sanitizing solutions 84a and 84b. The supply conduits 68 and 70 are connected directly to containers 86a and 86b, whereby pressure applied by hand or other means directly to containers 86a and 86b will cause sanitizing solutions 84a and 84b to flow through lines 68 and 70 to canister 56 where the two solutions combine to perform the sterilizing function.

The use of pre-packaged bags of sterilizing solution affords a high degree of quality control over the purity, strength and efficacy of the sterilizing agent. Such pre-packaged containers of sterilizing agent can easily be replaced by removing the lines 68 and 70 from a depleted bag of sterilizing solution and attaching lines 68 and 70 to a fresh bag of solution. Alternatively, the entire reservoir assembly 80 may be removed and replaced as a unit by disconnecting the lines 68 and 70 from a depleted bag of sterilizing solution, removing the reservoir assembly consisting of the housing 81, the pressure plate 82, and depleted sterilizing solution container 86, and inserting therefor a replacement reservoir assembly unit consisting of a new housing 81, plate 82 and pre-packaged container 86 of fresh sterilizing solution.

The sides 55 of toothbrush storage compartment 54 extend downwardly to engage and rest on the top surface of pressure plate 82 of the reservoir housing 81, whereby the application of a downward pressure on lid 12 will be transferred through the toothbrush storage compartment housing sides 55 to the reservoir pressure plate 82 to cause sterilizing solution 84 to flow through lines 68 and 70 to canister 56.

The preferred sterilizing solution 84 is a hypo chlorite, but alternative antiseptic solutions such as alcohol or any of the commercially available disinfectants non-injurious to oral tissues could be used to obtain the desired results.

It will be apparent that this invention is capable of application to store and sanitize a plurality of toothbrushes by providing a plurality of toothbrush storage canisters 56 which are each connected to the sanitizing solution reservoir 80 through conduits 68 and 70, and a lid 12 which has a number of slots 30 equal to the number of canisters 56 for receiving the handles of toothbrushes 2. It will also be apparent that a plurality of individual toothbrush holders each capable of holding and storing a single toothbrush may be mounted side-by-side on an appropriate mounting rack to provide the capability of holding and sanitizing a plurality of toothbrushes simultaneously.

The toothbrush holder and sanitizing flush apparatus of the present invention is illustrated and preferably constructed of plastic for durability and ease of maintenance and cleaning. However, other materials such as ceramics and glass could be used to obtain the desired results.

The toothbrush holder and sanitizing flush apparatus of the present invention is used by removing the lid 12 and inserting the bristles of a toothbrush through the bristle flexing member 50 and into the bottom of canister 56. The toothbrush handle 6 is then inserted into the slot 30 in lid 12 and the lid is then placed on toothbrush storage compartment 54. Then, a pressure on the top of lid 12 is transferred through storage compartment sides 55 to the reservoir pressure plate 82 to cause sufficient sanitizing solution 84 to be pumped through lines 68 and 70 to canister 56 to cover toothbrush bristles 4.

The canister 56 is flushed by opening the flush spout 57 to permit used sterilizing solution and food particles flexed from the bristles to drain from the canister while fresh sterilizing solution is pumped into the canister from reservoir 80. The addition of fresh sanitizing solution may be accomplished either simultaneously with or subsequently to the draining of used solution from canister 56.

This invention of a toothbrush holder and sanitizer flush apparatus provides a useful and hygienic apparatus for simultaneously storing and sanitizing toothbrushes between uses. It will be appreciated by those skilled in the art that changes could be made to the embodiments described above without departing from the inventive concept thereof. It is understood, therefore, that this invention is intended to cover all modifications which are within the spirit and scope of the invention as defined by the appended claims.

I claim:

1. Apparatus for storing and sanitizing a toothbrush comprising:

a housing consisting of a top section, a middle section and a bottom section, said top section being positioned on and removable from said middle section and said middle section being positioned on said bottom section;

said top section forming a removable lid on said middle section and having a slot for receiving the handle of a toothbrush;

a toothbrush storage canister in said middle section, said canister having an open top end and an enclosed bottom and being capable of holding a toothbrush in a substantially vertical position, whereby, when a toothbrush is positioned with its bristles at said canister bottom, the toothbrush handle will project through said open top for insertion in said top section slot;

said bottom section containing a reservoir of sterilizing solution; and fluid conduit means for connecting said reservoir to said canister to transfer sterilizing solution from said reservoir to said canister, whereby the bristles of said toothbrush are immersed in said sterilizing solution.

2. The apparatus of claim 1 further comprising:

a supply of disinfectant stored in said housing top section; and means for transporting said disinfectant to said slot, whereby said handle will be exposed to said disinfectant.

3. The apparatus of claim 1 further comprising:

a supply of disinfectant stored in said housing top section and packaged in a container having a porous wall, whereby said disinfectant will escape from said container by seepage; and means for transporting said disinfectant escaping from said porous container to said slot, whereby said handle will be exposed to said disinfectant.

4. The apparatus of claim 1 further comprising:

drain means positioned on said canister for selectively draining sanitizing solution from said canister.

5. The apparatus of claim 1 further comprising: a flexing member aligned with said canister open top end and capable of flexing the bristles of a toothbrush passing therethrough.

6. The apparatus of claim 1 further comprising a unidirectional flow valve in said fluid conduit means for permitting flow of said sterilizing solution from said reservoir to said canister and preventing flow of said sterilizing solution from said canister to said reservoir.

7. The apparatus of claim 1 wherein said reservoir for storing a supply of sterilizing solution is a deformable container of sterilizing solution and wherein a force applied to said housing top section is transmitted through said housing middle section to said housing bottom section to cause sterilizing solution to flow from said reservoir to said canister.

8. The apparatus of claim 1 wherein said reservoir for storing a supply of sterilizing solution is a plurality of deformable containers, each said deformable container having a different sterilizing solution therein, and wherein a force applied to said housing top section is transmitted through said housing middle section to said housing bottom section to cause sterilizing solution to flow from said reservoir to said canister.

9. Apparatus for storing and sanitizing a toothbrush comprising:

a removable lid having a slot for receiving the handle of a toothbrush, a bottom with a opening therein aligned with said slot, a chamber containing a supply of disinfectant, and means for absorbing and transporting said disinfectant to said slot, whereby a toothbrush handle in said slot will be exposed to said disinfectant;

a toothbrush storage compartment having a shelf for receiving and supporting said removable lid and a canister with an open top end, an enclosed bottom and means for draining sterilizing solution therefrom, said canister being capable of holding a toothbrush in a substantially vertical position, whereby, when a toothbrush is positioned with its bristles at said canister bottom, the toothbrush handle will project through said open top for insertion in said slot; and a reservoir capable of receiving and supporting said storage compartment, said reservoir containing a supply of sterilizing solution, and fluid conduit means connecting said supply of sterilizing solution to said canister, whereby pressure applied to said lid will be transmitted through said storage compartment to said reservoir to cause sterilizing solution to be supplied through said fluid conduit means to said canister.

10. The apparatus of claim 9 further comprising a porous wall on said chamber containing disinfectant, whereby disinfectant will escape from said chamber by seepage through said porous wall; and wherein said means for absorbing and transporting said disinfectant to said slot is a sponge in contact with said porous wall.

11. The apparatus of claim 9 further comprising a ring member aligned with said canister open top end and capable of flexing the bristles of a toothbrush passing through said ring member.

12. The apparatus of claim 9 wherein said means on said canister for receiving sterilizing solution comprises ports; and said means connecting said reservoir to said canister comprises fluid conduits connected to said ports.

13. The apparatus of claim 9 wherein said means for draining said sterilizing solution from said canister comprises a spout on said canister.

14. The apparatus of claim 9 wherein said reservoir comprises a deformable container of sterilizing solution.

15. The apparatus of claim 9 wherein said reservoir comprises a plurality of deformable containers which each contain a different sterilizing solution.

16. The apparatus of claim 9 wherein said reservoir contains a deformable container of sterilizing solution; said means on said canister for receiving sanitizing solution comprises ports on said canister; and said means connecting said reservoir to said canister comprise fluid conduits connecting said deformable container to said ports.

17. The apparatus of claim 9 wherein said chamber containing disinfectant comprises a porous container of disinfectant, whereby said disinfectant will escape by seepage from said porous container.

18. Apparatus for storing and sanitizing a toothbrush comprising:

a top housing section forming a removable lid having a slot therein for receiving the handle of a toothbrush;

a middle housing section forming a toothbrush storage compartment having an open top end and an enclosed bottom, said compartment being capable of holding a toothbrush in a substantially vertical position, whereby, when a toothbrush is positioned with its bristles at said compartment bottom, the toothbrush handle will project through said open top for insertion in said slot, said middle housing section being adapted to receive and support said top housing section;

a bottom housing section forming a reservoir having a plurality of containers of sterilizing solution, said bottom housing section being adapted to receive and support said middle housing section; and fluid conduit means for connecting each of said containers of sterilizing solution to said toothbrush storage compartment, whereby said sterilizing solutions may be selectively transferred to said storage compartment to sanitize the bristles of said toothbrush.

19. The apparatus of claim 18 wherein said reservoir comprises a plurality of deformable packages, with each said package containing a different sterilizing solution.

20. The apparatus of claim 18 further comprising: a supply of disinfectant in said top housing section; and means for transporting said disinfectant to said slot, whereby said handle will be exposed to said disinfectant.

* * * * *